United States Patent
Rizoiu et al.

(10) Patent No.: US 7,620,290 B2
(45) Date of Patent: Nov. 17, 2009

(54) MODIFIED-OUTPUT FIBER OPTIC TIPS

(75) Inventors: Ioana M. Rizoiu, San Clemente, CA (US); Jeffrey W. Jones, Robertson, WY (US); Dmitri Boutoussov, Dana Point, CA (US)

(73) Assignee: Biolase Technology, Inc., Irvine, CA (US)

( * ) Notice: Subject to any disclaimer, the term of this patent is extended or adjusted under 35 U.S.C. 154(b) by 440 days.

(21) Appl. No.: 11/033,441

(22) Filed: Jan. 10, 2005

(65) Prior Publication Data

US 2005/0281530 A1 Dec. 22, 2005

Related U.S. Application Data

(63) Continuation-in-part of application No. 10/404,683, filed on Apr. 1, 2003, now Pat. No. 7,187,822, which is a continuation of application No. 09/822,981, filed on Mar. 30, 2001, now Pat. No. 6,567,582, which is a continuation-in-part of application No. 09/469,571, filed on Dec. 22, 1999, now Pat. No. 6,389,193, and a continuation-in-part of application No. 09/256,697, filed on Feb. 24, 1999, now Pat. No. 6,350,123, which is a continuation-in-part of application No. 08/985,513, filed on Dec. 5, 1997, now abandoned, and a continuation-in-part of application No. 08/995,241, filed on Dec. 17, 1997, now abandoned, which is a continuation of application No. 08/522,503, filed on Aug. 31, 1995, now Pat. No. 5,741,247, which is a continuation of application No. 08/575,775, filed on Dec. 20, 1995, now Pat. No. 5,785,521.

(60) Provisional application No. 60/535,003, filed on Jan. 8, 2004, provisional application No. 60/622,645, filed on Oct. 26, 2004.

(51) Int. Cl.
G02B 6/10 (2006.01)
G02B 6/26 (2006.01)
A61B 17/32 (2006.01)
A61B 18/22 (2006.01)

(52) U.S. Cl. .......................... 385/146; 385/43; 604/22; 606/16; 606/167; 606/13

(58) Field of Classification Search ....................... None
See application file for complete search history.

(56) References Cited

U.S. PATENT DOCUMENTS 5,188,634 A 2/1993 Hussein et al.
5,257,991 A * 11/1993 Fletcher et al. ............... 606/17

(Continued)

OTHER PUBLICATIONS

International Search Report, May 25, 2006, PCT/US05/00851.

(Continued)

*Primary Examiner*—Omar Rojas
(74) *Attorney, Agent, or Firm*—Stout, Uxa, Buyan & Mullins, LLP

(57) ABSTRACT

A laser handpiece is disclosed, including a shaped fiber optic tip having a side-firing output end with a non-cylindrical shape. The shaped fiber optic tip can be configured to side-fire laser energy in a direction away from a laser handpiece and toward sidewalls of a treatment or target site.

10 Claims, 11 Drawing Sheets

U.S. PATENT DOCUMENTS

| | | | | |
|---|---|---|---|---|
| 5,303,324 | A * | 4/1994 | Lundahl | 385/147 |
| 5,428,699 | A * | 6/1995 | Pon | 385/31 |
| 5,497,441 | A * | 3/1996 | Croitoru et al. | 385/125 |
| 5,772,657 | A * | 6/1998 | Hmelar et al. | 606/15 |
| 5,785,645 | A | 7/1998 | Scheller | |
| 5,836,941 | A * | 11/1998 | Yoshihara et al. | 606/15 |
| 5,953,477 | A * | 9/1999 | Wach et al. | 385/115 |
| 5,968,037 | A * | 10/1999 | Rizoiu et al. | 606/13 |
| 6,129,721 | A * | 10/2000 | Kataoka et al. | 606/2 |
| 6,304,688 | B1 | 10/2001 | Korn et al. | |
| 6,343,174 | B1 * | 1/2002 | Neuberger | 385/123 |
| 6,620,153 | B2 * | 9/2003 | Mueller et al. | 606/15 |
| 6,669,687 | B1 | 12/2003 | Saadat | |
| 6,802,838 | B2 * | 10/2004 | Loeb et al. | 606/13 |
| 2005/0256517 | A1 | 11/2005 | Boutoussov | |
| 2005/0281530 | A1 | 12/2005 | Rizoiu et al. | |

OTHER PUBLICATIONS

International Search Report, Aug. 1, 2008 PCT/US08/52106.

* cited by examiner

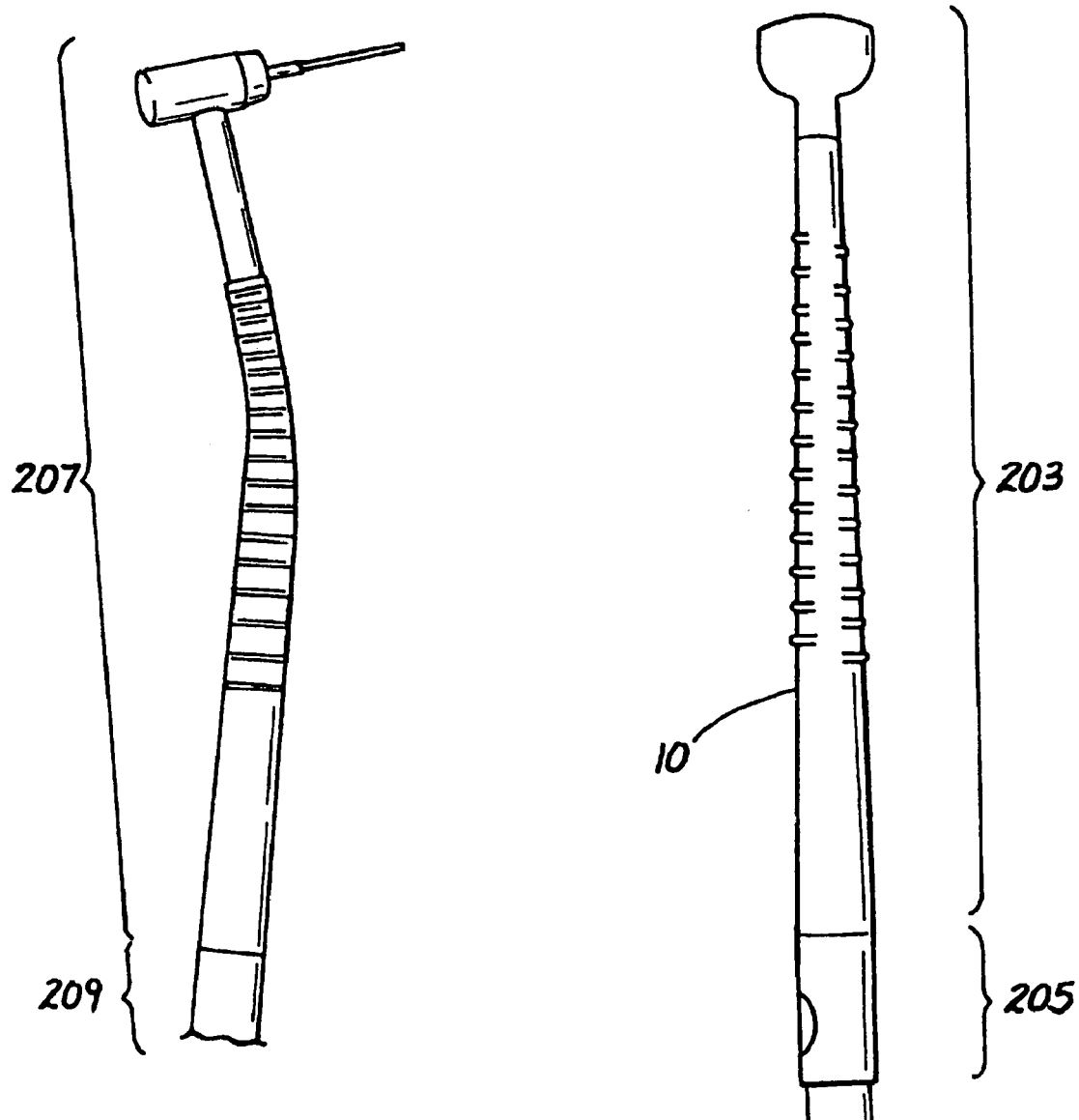

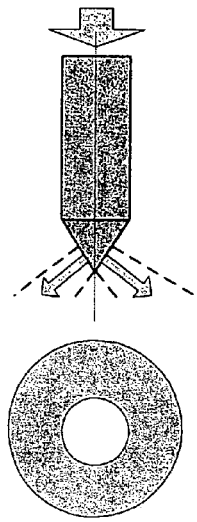 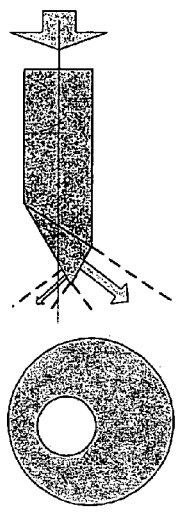 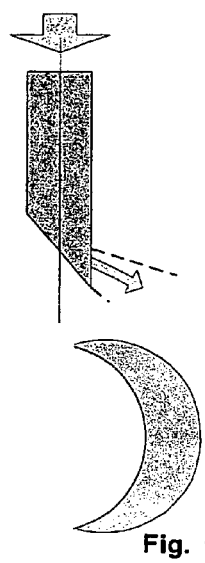
Fig 10a    Fig.10c    Fig. 10d
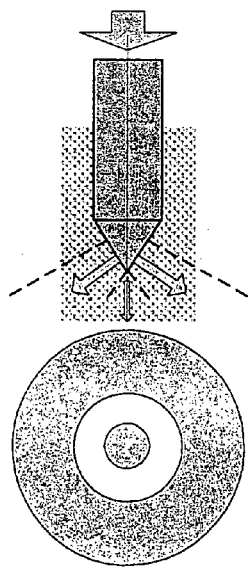
Fig. 11

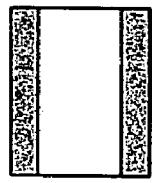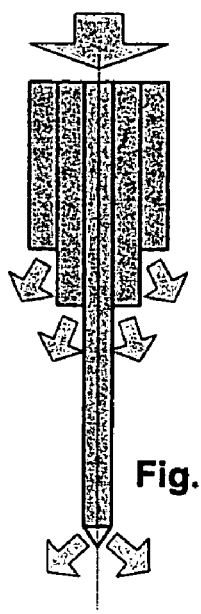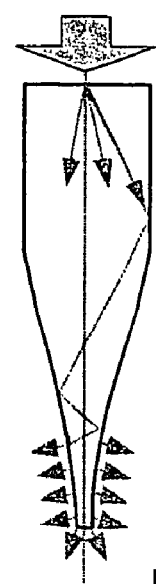
Fig. 12a
Fig. 12b
Fig. 13

MODIFIED-OUTPUT FIBER OPTIC TIPS

CROSS-REFERENCE TO RELATED APPLICATIONS

The application claims the benefit of U.S. Provisional Application No. 60/535,003, filed on Jan. 8, 2004, and U.S. Provisional Application No. 60/622,645, filed Oct. 26, 2004, the entire contents of both which are incorporated herein by reference. This application is a continuation-in-part of U.S. application Ser. No. 10/404,683, filed Apr. 1, 2003 now U.S. Pat. No. 7,187,822, which is a continuation of U.S. application Ser. No. 09/822,981, filed Mar. 30, 2001, (now U.S. Pat. No. 6,567,582), which is a continuation-in-part of U.S. application Ser. No. 09/469,571, filed Dec. 22, 1999, (now U.S. Pat. No. 6,389,193), and of U.S. application Ser. No. 09/256,697, filed Feb. 24, 1999, (now U.S. Pat. No. 6,350,123), both of which are commonly assigned and the contents of which are expressly incorporated herein by reference. U.S. application Ser. No. 09/256,697 is a continuation-in-part of U.S. application Ser. No. 08/985,513, filed Dec. 5, 1997, now abandoned, which is a continuation of U.S. application Ser. No. 08/522,503, filed Aug. 31, 1995, (now U.S. Pat. No. 5,741,247), and is a continuation-in-part of U.S. application Ser. No. 08/995,241, filed Dec. 17, 1997, now abandoned, which is a continuation of U.S. application Ser. No. 08/575,775, filed Dec. 20, 1995, (now U.S. Pat. No. 5,785,521), all of which are commonly assigned and the contents of which are expressly incorporated herein by reference.

BACKGROUND OF THE INVENTION

1. Field of the Invention

The present invention relates generally to medical devices and, more particularly, to fiber optic tips for delivering electromagnetic radiation.

2. Description of the Related Art

Fiber optics have existed in the prior art for delivering electromagnetic radiation. Radiation delivery systems are typically used to transport electromagnetic radiation from electromagnetic energy sources to treatment sites. One common radiation delivery system can comprise a cylindrically-shaped fiber optic tip from which electromagnetic radiation is emitted in a direction toward the treatment site.

In certain applications, radiation delivery systems can be engineered to generate predetermined beam shapes and spatial energy distributions. The energy distribution of a simple delivery system, comprising a fiber optic tip, can be described as having a circular illumination area, with a so-called Gaussian distribution of beam intensities being spatially distributed within the output beam pattern or illuminated area. For instance, the output beam pattern from a fiber optic tip can comprise a central high-intensity area or "hot spot" surrounded by peripheral areas of lower intensity.

Regarding energy distributions, some beam profiling applications can require or would be optimized with radiation delivery systems capable of generating illumination distributions that vary across parts or all of the illumination area surrounding the output of the radiation delivery system. Moreover, it may also be desirable to generate non-circular illumination areas, or to generate electromagnetic radiation having predetermined energy distributions across a non-planar illumination area. Use of laser radiation having a relatively uniform power distribution over a particularly shaped area can be a practical task for multiple medical applications.

SUMMARY OF THE INVENTION

The present invention provides optical arrangements and relatively compact medical laser instruments to deliver electromagnetic radiation to treatment sites with power distributions that vary in a non-Gaussian distribution fashion, compared to cylindrical output fibers, across parts or all of the illumination area surrounding the output waveguide. The illumination areas may comprise curved surfaces, such as cavities, in which case substantial output power densities can be concentrated on sidewalls of the illumination areas. The electromagnetic radiation can comprise laser radiation, and the treatment site can comprise tissue to be treated.

The various embodiments of the present invention may include or address one or more of the following objectives. One objective is to provide a fiber optic tip having a shaped fiber optic output end (i.e., a fiber optic output end not consisting only of a planar surface orthogonal to the fiber optic axis) for delivery of electromagnetic radiation, wherein electromagnetic radiation exiting the fiber optic output end is not concentrated along the fiber optic axis. Another objective is to provide a fiber optic output end having an emission characteristic whereby electromagnetic radiation exiting the fiber optic output end is relatively weak along the fiber optic axis. Yet another object is to provide a fiber optic output end wherein all waveguide modes experience total internal reflection on a first surface of the fiber optic output end and go out through an opposite surface of the fiber optic output end. Still another objective is to provide a apparatus for directing laser energy and fluid to different target sites through different reflections within a fiber conduit and from the fiber conduit to the output end or sites, wherein different energy distributions can be provided to different treatment surfaces surrounding or in a vicinity to the fiber conduit at the same time.

Any feature or combination of features described herein are included within the scope of the present invention provided that the features included in any such combination are not mutually inconsistent as will be apparent from the context, this specification, and the knowledge of one of ordinary skill in the art. For purposes of summarizing the present invention, certain aspects, advantages and novel features of the present invention have been described herein. Of course, it is to be understood that not necessarily all such aspects, advantages or features will be embodied in any particular embodiment of the present invention. Additional advantages and aspects of the present invention are apparent in the following detailed description and claims.

BRIEF DESCRIPTION OF THE DRAWINGS

FIGS. 3a-6 are other views of the structure;

FIG. 10a is cross-sectional view of a fiber optic tip comprising a conical side-firing output end in accordance with an embodiment of the present invention;

FIG. 10c is cross-sectional view of a fiber optic tip comprising an asymmetric conical side-firing output end, having an off-axis conical shape, in accordance with another embodiment of the present invention;

FIG. 10d is a cross-sectional view of a fiber optic tip comprising a bevel-cut side-firing output end according to a modified embodiment of the present invention;

FIG. 11 is cross-sectional view of a fiber optic tip comprising a conical side-firing output end which is constructed similarly to that of FIG. 10a and which is shown operated in an aqueous-environment;

FIG. 12a is an exploded, cross-sectional view of a multi-capillary fiber optic tip;

FIG. 12b is a cross-sectional view of an assembled multi-capillary fiber optic tip;

FIG. 13 is a cross-sectional view of a tapered fiber optic tip implementing a tapered side-firing output end;

DETAILED DESCRIPTION OF THE PRESENT INVENTION

Figure 1:
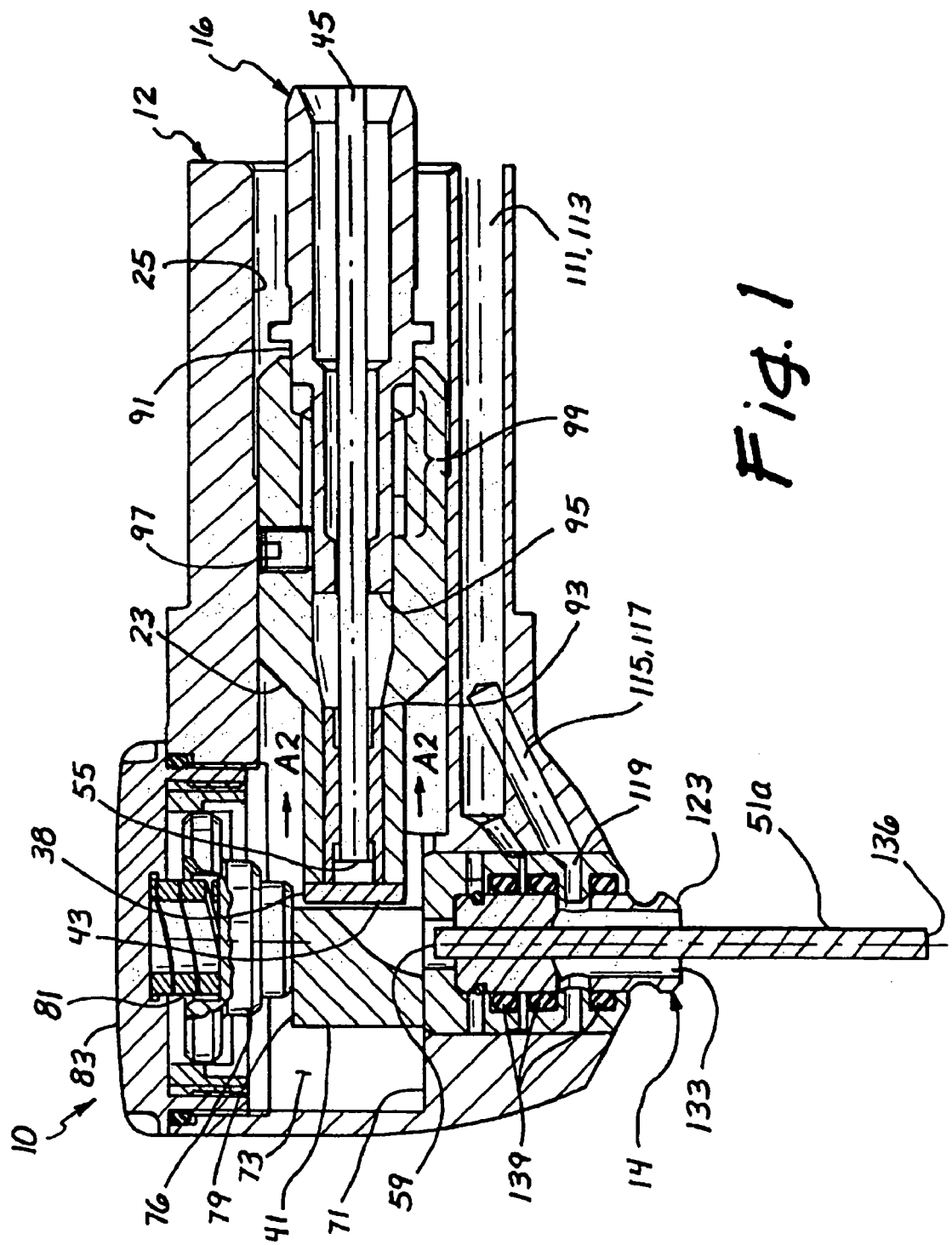
FIG. 1 is a cross-sectional view of a rotating handpiece.

Reference will now be made in detail to certain embodiments of the invention, examples of which are illustrated in the accompanying drawings. Wherever possible, the same or similar reference numbers are used in the drawings and the description to refer to the same or like parts. It should be noted that the drawings are in simplified form and are not to precise scale. In reference to the disclosure herein, for purposes of convenience and clarity only, directional terms, such as, top, bottom, left, right, up, down, over, above, below, beneath, rear, and front, are used with respect to the accompanying drawings. Such directional terms should not be construed to limit the scope of the invention in any manner.

Although the disclosure herein refers to certain illustrated embodiments, it is to be understood that these embodiments are presented by way of example and not by way of limitation. The intent of the following detailed description, although discussing exemplary embodiments, is to be construed to cover all modifications, alternatives, and equivalents of the embodiments as may fall within the spirit and scope of the invention as defined by the appended claims.

Referring more particularly to the drawings, FIG. 1 illustrates a cross sectional view of the rotating handpiece 10. The rotating handpiece comprises a handpiece head 12, a fiber tip fluid output device 14, and a removable trunk fiber assembly 16. These components can be seen in a partially disassembled state in FIG. 3, wherein the axis 18 of the removable trunk fiber assembly 16 is aligned with the axis 20 of the handpiece head 12 for insertion into the handpiece head 12. Once the axis 18 of the removable fiber assembly 16 is aligned with the axis 20 of the handpiece 12, the removable trunk fiber assembly 16 is moved in the direction of the arrow A1 into the handpiece head 12, while the axes 18 and 20 are maintained in approximate alignment. The contacting surface of the outer surface of the chuck 23 engages the inner surface 25 of the rotating handpiece 10, to thereby ensure alignment of the axis 18 of the removable trunk fiber assembly 16 and the axis 20 of the handpiece head 12. As the removable trunk fiber assembly 16 is inserted further in the direction A1 into the handpiece 12, the abutting surface 28 engages with a corresponding abutting surface (not shown) within the collar 31 of the handpiece head 12. The corresponding abutting surface 28 can be constructed to snap with the abutting surface 31, as the removable trunk fiber assembly 16 is fully inserted into the handpiece head 12. Any type of locking engagement between the abutting surface 28 and a corresponding abutting surface within the collar 31, as known in the art, may be used to ensure that the removable trunk fiber assembly 16 is always inserted the same distance into the handpiece head 12. As shown in FIG. 1, the distal tip 38 of the removable trunk fiber assembly 16 is brought into close proximity with the parabolic mirror 41. In the illustrated embodiment, the distal tip 38 of the removable trunk fiber assembly 16 comprises a window 43 for protecting the trunk fiber optic 45 from contaminants, such as water. In the alternative embodiment shown in FIG. 2, the distal tip 38a is not protected with a window. As shown in FIG. 1, the fiber tip 51 of the fiber tip fluid output device 14 is also accurately placed in close proximity to the parabolic mirror 41. A loading tool 17 can be used to assist in the placement of the fiber tip fluid output device 14 into the handpiece head 12, as discussed below with reference to FIGS. 5 and 7-9. Electromagnetic radiation exiting from the output end 55 of the trunk fiber optic 45 is collected by the parabolic mirror 41 and, subsequently, reflected and focused onto the input end 59 of the fiber tip 51.

Figure 4A:
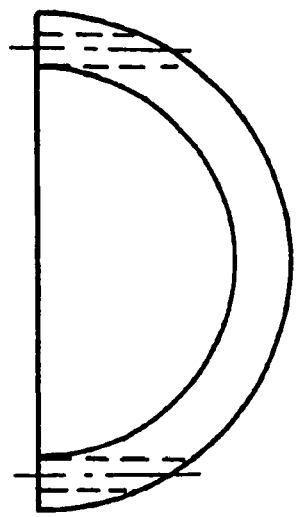
Figure 4B:
Figure 4C:
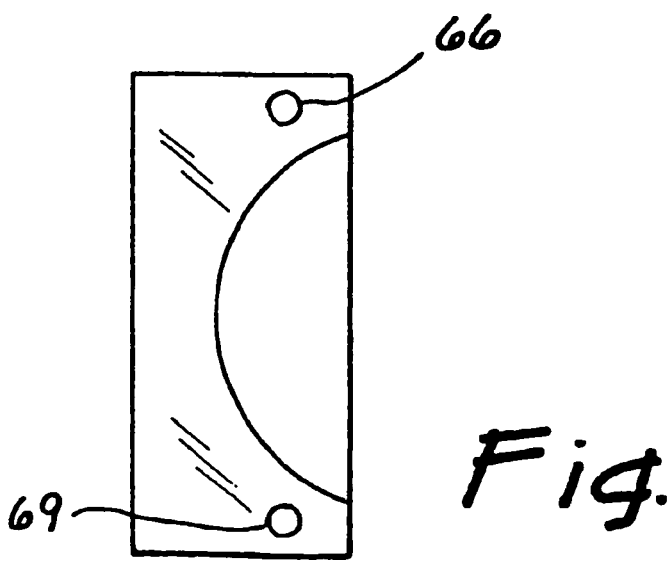

In one embodiment, the electromagnetic radiation exiting from the output end 55 of the trunk fiber optic 45 comprises a wavelength on the order of 3 microns. In other embodiments, electromagnetic radiation can be supplied at wavelengths from about 0.4 micron to about 11 microns, and in typical embodiments from about 0.4 micron to about 3 microns, from a light source such as a plasma arc lamp, a LED, or a laser having a continuous wave (CW) or pulsed mode of operation. The material of the parabolic mirror 41 is selected to provide an efficient reflection and focusing into the input end 59. As presently embodied, the electromagnetic radiation is generated from an Er:YSGG laser, and the material of the parabolic mirror 41 comprises a gold plating to provide reflectivity of approximately 99.9 percent. Other materials may be selected in accordance with design parameters. Other reflective surfaces and materials for the parabolic mirror 41 may be selected, in accordance with the laser being used and the desired efficiency of reflection. For example, if a lower reflectivity is selected, then additional cooling may be needed for the parabolic mirror 41 (such as a greater flow rate of cooled and/or filtered air across the surface of the parabolic mirror 41). FIGS. 4a, 4b and 4c illustrate various views of the parabolic mirrors 41 of the presently illustrated embodiment. The flat surface of the parabolic mirror 41, which is closest to the fiber tip 51, can be provided with two recessed areas 66 and 69. These two recessed areas mate with corresponding protrusions (not shown) on the floor 71 of the internal chamber 73 of the handpiece head 12. A spring loaded plunger 76 presses against the upper surface 79 of the parabolic mirror 41 under the pressure of the spring 81. A screw cap 83 holds the spring 81 against the spring loaded plunger 76. The combination of the spring loaded plunger 76, the recessed areas 66,69 of the parabolic mirror 41, and the corresponding protrusions on the floor 71, together, accurately align the parabolic mirror 41 for efficient coupling of electromagnetic radiation between the output end 55 of the trunk fiber optic 45 and the input end 59 of the fiber tip 51. In modified embodiments, either or both of the output end 55 of the trunk fiber optic 45 and the input end 59 of the fiber tip 51 is/are provided with an anti-reflective coating. Although it may be preferred in certain implementations to have the trunk fiber optic 45 perfectly aligned in relation to the parabolic mirror 41 and the fiber tip 51, the alignment between these three elements is seldomly perfect. In the presently illustrated embodiment, the misalignment of the axis of the trunk fiber optic 45 and the axis of the fiber tip 51 is within plus or minus 1 percent error.

In a modified embodiment, a pentaprism (five-sided prism) is used instead of the parabolic mirror 41 for coupling the trunk fiber optic 45 to the fiber tip 51. In addition to slight misalignment of the axis of the trunk fiber optic 45, slight imperfections on the output end 55 of the trunk fiber optic 45 may also be present. The parabolic mirror 41 corrects for both of these slight errors, by collecting the electromagnetic radiation from the output end 55 of the front fiber optic 45 and, subsequently, focusing the electromagnetic radiation into the input end 55 of the fiber tip 51.

The parabolic mirror 41 may also comprise molypdium, in an exemplary embodiment. The clamp assembly 91 operates to firmly grip and hold the trunk fiber optic 45. In the presently illustrated embodiment, the clamp assembly 91 is provided with at least one slit, which extends from the distal end 93 of the clamp assembly 91 to a region 95 just distal of the set screw 97. As presently embodied, the at least one slit extending from the distal end 93 to the region 95 just distal of the set screw 97 comprises two slits, which are adapted to allow the clamp assembly 91 to be compressed by the chuck 23 onto the trunk fiber optic 45. The chuck 23 thus presses against the portion of the clamp assembly 91, wherein the portion is defined between the distal end 93 and the region 95, to thereby have the clamp assembly 91 squeeze and hold the trunk fiber optic 45 in place. In the presently illustrated embodiment, the set screw 97 is used to hold the chuck 23 in place and prevent rotation thereof. In the illustrated embodiment, the outer surface of the clamp assembly 91 is provided with threads 99 for engaging with corresponding threads on the inner surface of the chuck 23. In the illustrated embodiment, the chuck 23 is screwed onto the threads of the clamp assembly 91, before the removable trunk fiber assembly 16 is inserted into the handpiece 12. The chuck 23 is screwed onto the clamp assembly 91 to a predetermined tightness, and then the set screw 97 is secured thereto to securely hold the chuck 23 to the clamp assembly 91. Subsequently, the removable trunk fiber assembly 16 is inserted and secured into the handpiece head 12.

Referring to FIGS. 5 and 7-9, the fiber tip fluid output device 14 comprises a generally cylindrical body having an outer surface, a proximal end, a distal end, and a lumen extending between the proximal end and the distal end. The lumen is sized and shaped to accommodate the fiber tip 51a therethrough so that the fiber tip 51a extends through the lumen from the proximal end to the distal end of the generally cylindrical body. The fiber tip fluid output device 14 further comprises a plurality of apertures 125 extending around the generally cylindrical body. Each of the apertures 125 fluidly connects the outer surface to the lumen. As presently embodied, the lumen comprises a first diameter near the proximal end and a second diameter near the distal end, wherein in the illustrated embodiment the second diameter is greater than or equal to about two times the first diameter. As presently embodied, the lumen comprises a proximal lumen section and a distal lumen section, the proximal lumen section having a diameter which in the illustrated embodiment is equal to the first diameter and the distal lumen section having a diameter which in the illustrated embodiment is equal to the second diameter. The proximal lumen section comprises a proximal end, a distal end, and a lumen axis extending between the proximal end and the distal end; the distal lumen section comprises a proximal end, a distal end, and a lumen axis extending between the proximal end and the distal end; and the diameter of the proximal lumen section in the illustrated embodiment can be substantially constant along a length of the proximal lumen section between the proximal end of the proximal lumen section and the distal end of the proximal lumen section. The diameter of the distal lumen section can be substantially constant along a length of the distal lumen section between the proximal end of the distal lumen section and the distal end of the distal lumen section. In the illustrated embodiment, the first diameter transitions to the second diameter at the distal end of the proximal lumen section and the proximal end of the distal lumen section, a distal opening of the fiber tip fluid output device 14 has a diameter which is equal to the second diameter, and a proximal opening of the fiber tip fluid output device 14 has a diameter which is equal to the first diameter. In the illustrated embodiment, each of the apertures 125 has a diameter which is about half of the first diameter.

The apertures 125 can be disposed within a first depression 121. A second depression extends around the generally cylindrical body near the proximal end, and a third depression extends around the generally cylindrical body near the distal end, wherein the first depression is disposed about half way between the second depression and the third depression in the illustrated embodiment. As presently embodied, the distal lumen section tapers into the proximal lumen section along a length of the lumen that in the illustrated embodiment is equal to about one third of at least one of the cross-sectional diameters of the apertures 125.

Figure 5A:
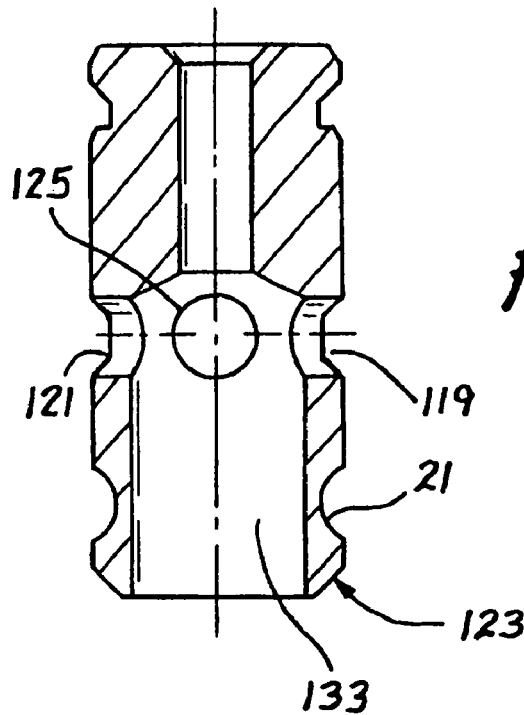
Figure 5B:
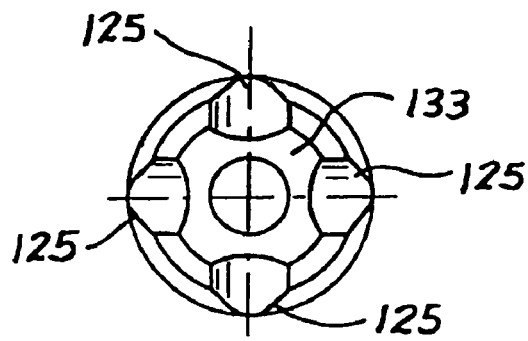
Figure 5C:
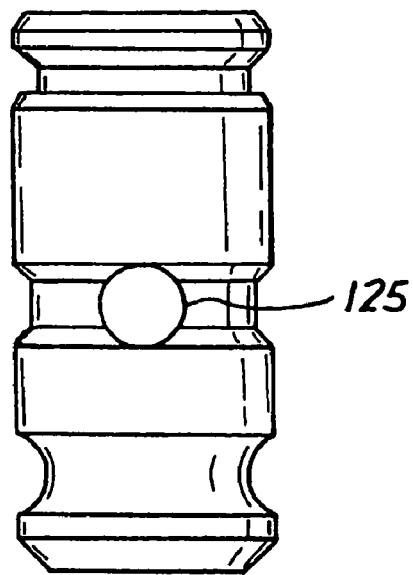

The rotating handpiece 10 of the illustrated embodiment can use the electromagnetically induced cutting system disclosed in U.S. Pat. No. 5,741,247, the entire contents of which are expressly incorporated herein by reference. For example, an engineered and controllable atomized distribution of fluid particles is placed into an interaction for absorption of electromagnetic radiation (from the fiber tip 51a) and for subsequent expansion to impart mechanical cutting forces onto a target or treatment surface. In the illustrated embodiment of FIG. 1, separate air and fluid lines 111, 113, which may be similar to those described in U.S. Pat. No. 5,741,247, run parallel to one another in the distal direction toward the feed channels 115, 117. In other embodiments, the air and fluid lines 111, 113 may comprise a first fluid line for carrying a first fluid and a second fluid line for carrying a second fluid, and further may comprise one or more additional fluid lines (not shown). Thus, while the illustrated embodiment describes the first fluid being air and the second fluid being water, the present disclosure is not limited to such structure and use. For example, the first and second fluids, and additional fluids, may comprise any of the components described in U.S. Pat. No. 5,785,521, the entire contents of which are expressly incorporated herein by reference. Some or all of the components of U.S. Pat. No. 5,785,521 may be premixed and carried through fluid lines, such as the lines 115, 117, or not premixed and mixed within the circumferential chamber 119 discussed below. The feed channels 115, 117, carrying a supply of air and water, respectively, as presently embodied, feed into circumferential chamber 119. Referring to FIGS. 5a-5c, the circumferential chamber 119 can be formed in a first depression 121 of the fiber tip ferrule 123. In an alternative embodiment, the section 121 may not have any depression.

As can be seen from FIG. 5b, for example, four apertures 125 are disposed in the first depression 121 of the fiber tip ferrule 123. In modified embodiments, other numbers of apertures may be incorporated. Air traveling into the circumferential chamber 119 from the feed channel 115, and water traveling into the circumferential chamber 119 from the feed channel 117, are both initially mixed in the circumferential chamber 119. In one embodiment, the first and second fluids may comprise air and a medicated or flavored water, and in another embodiment the first and second fluids may comprise water and at least one other fluid. In still another embodiment, at least one of the first and second fluids may comprise a medicament, such as chlorhexidine gluconate.

The initially-mixed air and water travel from the circumferential chamber 119 through the orifices 125 and into the lumen 133. The air and water is further mixed and atomized within the lumen 133. The atomized water under air pressure subsequently travels along the fiber tip 51 in a direction toward the output end 136 of the fiber tip 51. In a typical embodiment, the fiber tip 51a is permanently affixed to and extends through the fiber tip fluid output device 14. As presently embodied, three O-ring seals 139 are provided to seal the inside of the rotating handpiece from the air and water.

Figure 7:
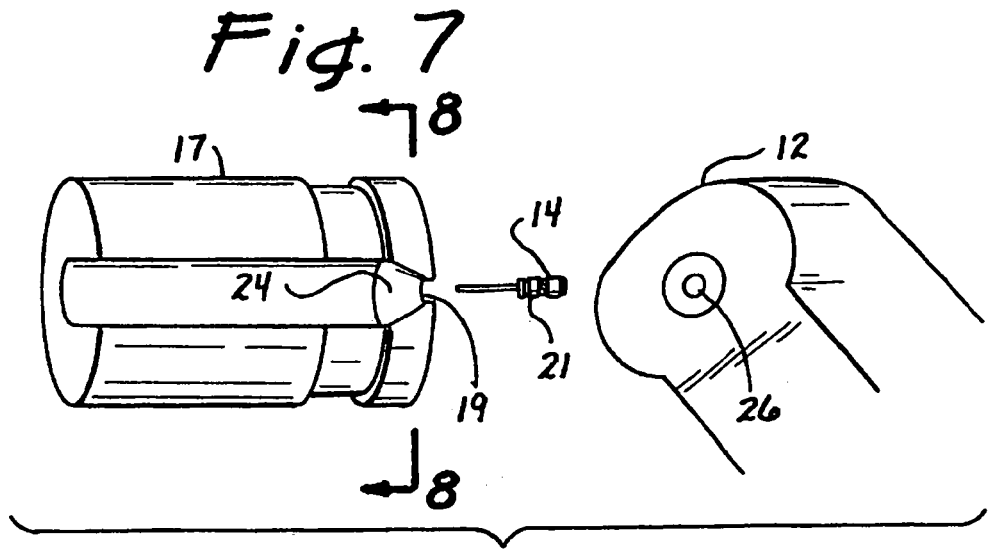
FIG. 7 is a perspective view of the loading tool, fiber tip fluid output device, and handpiece head in a disassembled configuration.
Figure 8:
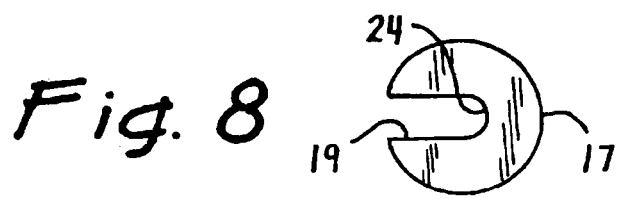
FIG. 8 is an end view of the loading tool, taken along the line 8-8 of FIG. 7.

FIG. 7 illustrates the loading tool 17, the fiber tip fluid output device 14, and handpiece head 12 in a disassembled configuration, and FIG. 8 is an end view of the loading tool 17, taken along the line 8-8 of FIG. 7.

Figure 9:
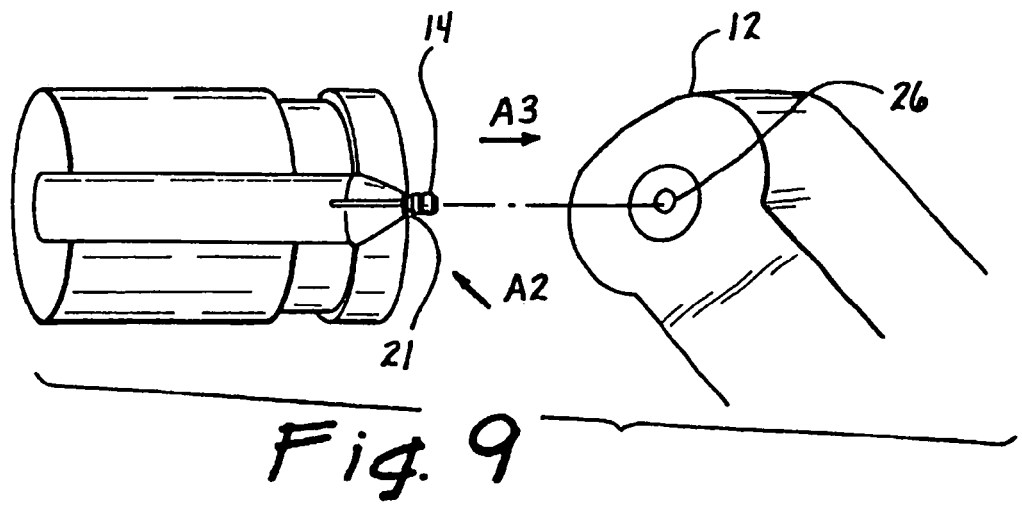
FIG. 9 is a perspective view of the fiber tip fluid output device partially secured onto the loading tool, just before insertion of the fiber tip fluid output device into the handpiece head.

FIG. 9 shows the fiber tip fluid output device 14 partially secured onto the loading tool 17. The proximal end of fiber tip fluid output device 14 can be gripped by the hand of a user and slid into the slot 19 of the loading tool 17 in the direction of the arrow A2. As presently embodied slot 19 fits around the third depression 21 of the fiber tip fluid output device 14, and the fiber tip fluid output device 14 is slid within the slot 19 in the direction of the arrow A2 until the fiber tip fluid output device 14 reaches the end 24 of the slot 19. The loading tool is then advanced in the direction of the arrow A3 to firmly secure the fiber tip fluid output device 14 into the orifice 26 of the handpiece head 12. The loading tool 17 is then removed from the fiber tip fluid output device 14 to leave the fiber tip fluid output device 14 firmly secured within the orifice 26. As presently embodied, a width of the slot 19 is slightly larger than a diameter of the third depression 21, so that the fiber tip fluid output device 21 can be removably and snugly held by the loading tool 17.

Figure 2:
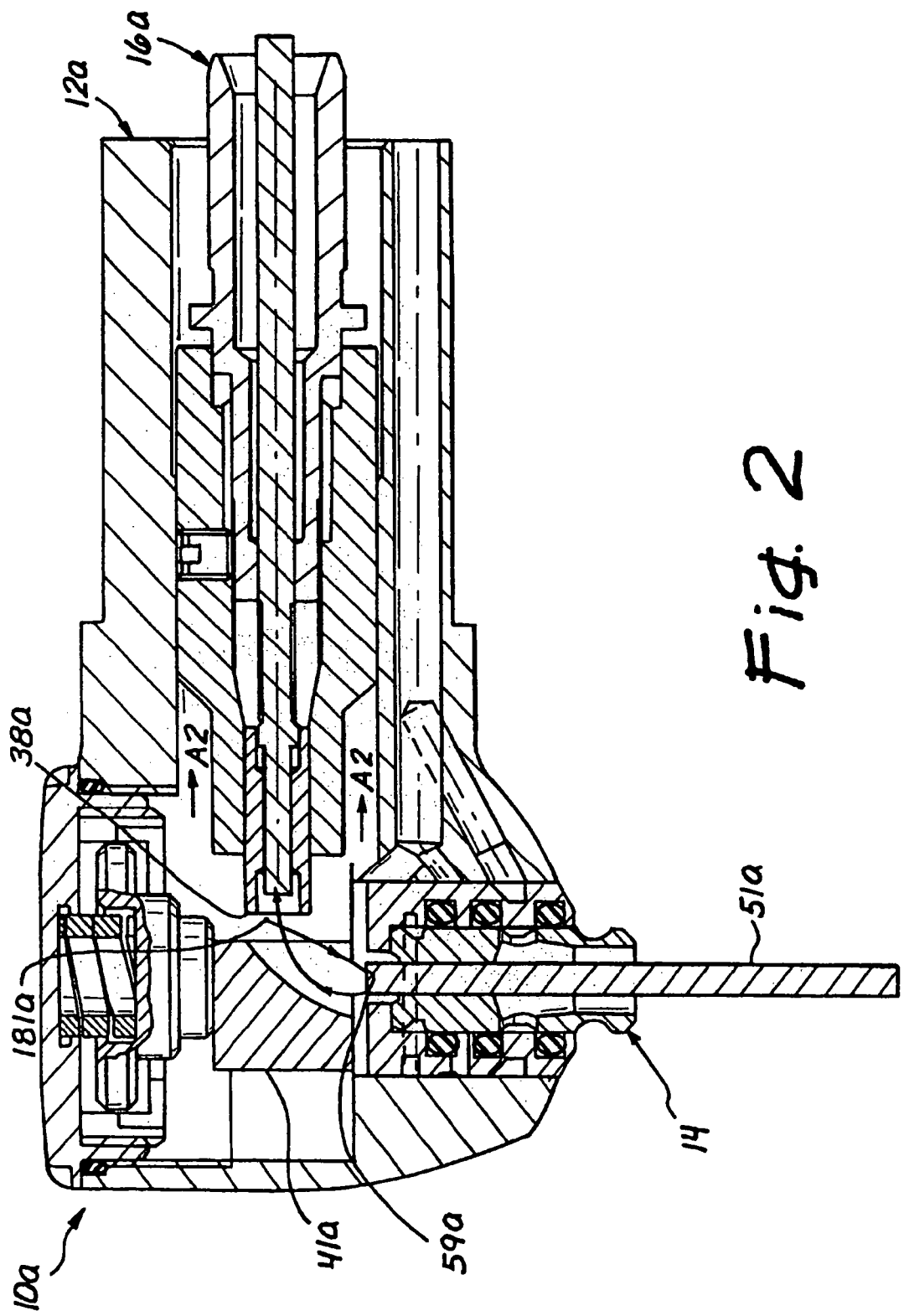
FIG. 2 is a cross-sectional view of an alternative embodiment of the rotating handpiece.
Figure 3:
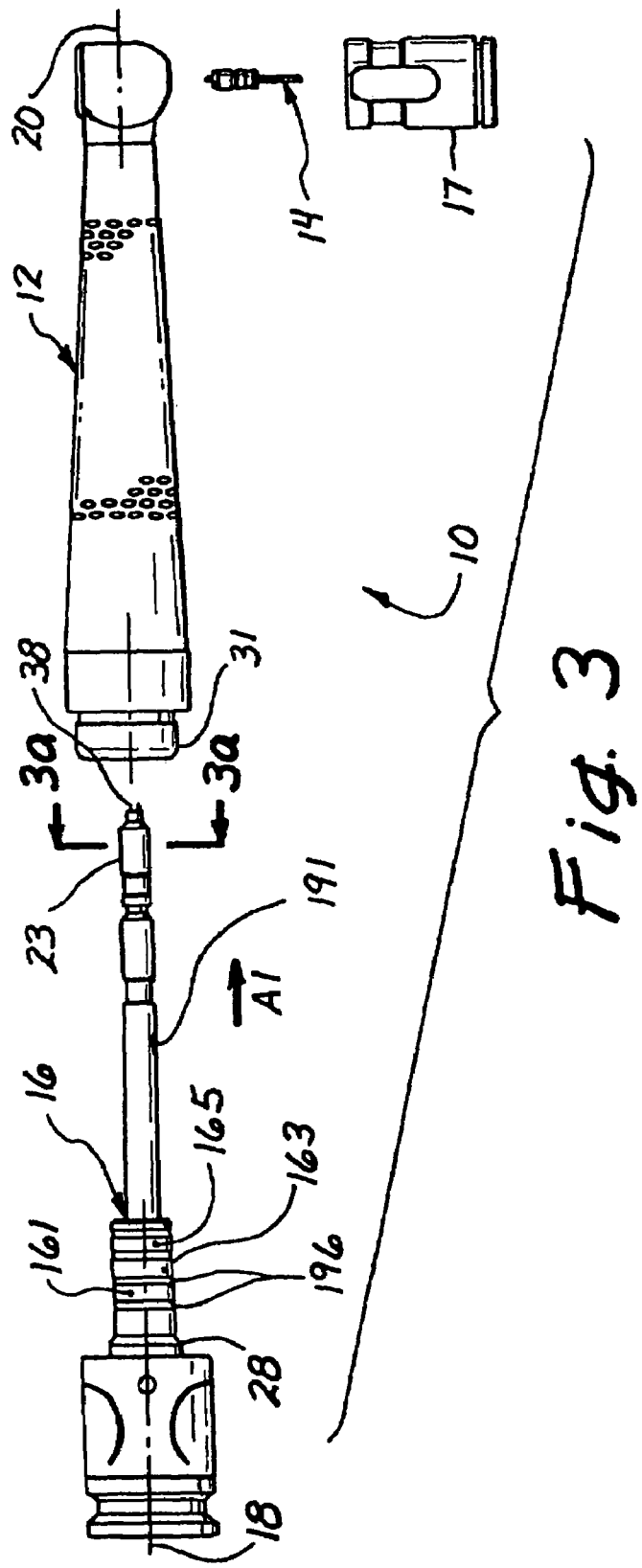
FIG. 3 is a side elevation view of the rotating hand piece in a partially disassembled state.
Figure 3A:
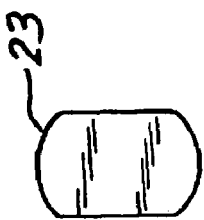

Referring to FIG. 3, the removable trunk fiber assembly 16 can be provided with three radial ports for introducing air, water, and (optionally) cooling air. More particularly, a fluid radial channel 161 feeds fluid (e.g., water) into the fluid channel 111, an air radial channel 163 feeds air into the air channel 113, and an optional cooling-air radial channel 165 feeds cooling air along a cooling-air channel, which exits in close proximity to the parabolic mirror 41. In a representative embodiment, the exit angle of the cooling air channel directs cooling air directly onto the parabolic mirror 41, so that the cooling air is reflected from the parabolic mirror 41 onto the input end 59 of the fiber tip 51 and, subsequently, onto the window 43. In FIG. 2, the cooling air exits from an orifice 181a and is channeled directly onto the input end 59a of the fiber tip 51a. Subsequently, the air is directed onto the parabolic mirror 41 and reflected onto the output end 55 of the trunk fiber optic 45. This configuration could also be implemented for the system of FIG. 1, wherein the cooling air subsequently is directed onto the window 43. Alternatively, in the embodiment of FIG. 2, the cooling air exiting the orifice 181a can be channeled directly onto the parabolic mirror 41, focusing onto the input end 59a of the fiber tip 51. In the embodiments of both FIG. 1 and FIG. 2, the cooling air is subsequently channeled in the direction of the arrows A2 through channels formed in the chuck 23. As shown in FIG. 3a, the chuck 23 can have portions of its two sides removed, to thereby form channels for passage of the cooling air. The cooling air travels through the channels of the chuck 23 under a vacuum pressure and, subsequently, is drawn into a removal port 191. Upon entering the removal port 191 under the vacuum, the cooling air travels in a direction opposite to the arrow A1 and exits the removal trunk fiber assembly 16. The four O-rings 196 insulate the radial channels 161, 163, 165 from one another.

FIG. 6a illustrates a side elevation view of the assembled rotating handpiece 10 and FIG. 6b illustrates a modified embodiment of the rotating handpiece 10, wherein the neck is slightly bent. In FIG. 6a the portion indicated by reference numeral 203 is adapted to rotate about an axis of the rotating handpiece 10. The portion 205 does not rotate. Similarly, in FIG. 6b, the portion 207 is adapted to rotate about an axis of the rotating handpiece, and the portion 209 docs not rotate. In the embodiment of FIG. 6b, the trunk fiber optic is configured to be slightly flexible, since the trunk fiber optic will need to bend and flex as the portion 207 is rotated relative to the portion 209. In either of the embodiments of FIGS. 6a and 6b, the user holds the rotating portion (203 or 207) with his or her thumb and two fingers (such as is conventional in the art) and allows the stationary portion (205 or 209) to rest on a portion of the hand bridging the user's forefinger and thumb. The three fingers holding the rotating portion (203 or 207) contact the rotating portion and can rotate the rotating portion, as the fixed portion (205 or 209) does not rotate and rests on the portion of the hand bridging the hand and the forefinger.

The following figures show exemplary embodiments of radiation emitting apparatuses which are constructed to emit electromagnetic radiation in non-centered or non-concentrically focused manners, relative to the output from a cylindrically-shaped fiber optic end (i.e., a truncated fiber end), onto target surfaces or treatment sites. The target surface or treatment site can comprise, for example, a part of the body, such as a tooth, a knee, a wrist, or a portion of the jaw to be treated.

The output radiation can be engineered to have a spatial energy distribution which differs from the spatial energy distribution of a conventional truncated fiber end. More particularly, in accordance with an aspect of the present invention, a radiation emitting apparatus is constructed to generate output radiation having a spatial energy distribution with one or more energy concentrations or peaks located in areas other than a center of the spatial energy distribution. The center of the spatial energy distribution can be defined as an area aligned with (or intersecting) an optical fiber axis of the shaped fiber optic tip or an area aligned with (or intersecting) an average direction of propagation of the output radiation. According to one aspect, the center of the spatial energy distribution can be defined as a central part of a cross-section of the output radiation taken in a direction orthogonal to the direction of propagation of the output radiation.

With particular reference to FIG. 10a, a cross-sectional view of a shaped fiber optic tip comprising a conical side-firing output end in accordance with an embodiment of the present invention is shown. The side-firing output end is depicted comprising a conical shape that tapers in an output direction of propagation of electromagnetic radiation. In a typical embodiment, the side-firing output end is polished to a symmetric, or substantially symmetric, conical shape to, for example, attenuate or avoid undesirable phenomena such as masking and power losses. For example, the shaped fiber optic tip may be grasped and moved to position a distal end thereof onto an operative surface of a polishing machine. The distal end of the shaped fiber optic is then oriented with respect to the operative surface, and rotated at a steady rate to remove portions of the fiber in an even fashion about the fiber optic axis, to thereby polish the distal end of the shaped fiber optic tip into a conical side-firing output end. The shaped fiber optic tip may comprise, for example, sapphire, diamond, or quartz (glass).

In accordance with an aspect of the present invention, all beams of laser radiation exit from the side-firing output end at relatively high angles of up to 90 degrees with respect to the fiber optic axis. Consequently, as presently illustrated in the example of a conical side-firing output end transmitting into air, a dark "blind spot" is formed in front of the side-firing output end such that the output beam pattern or illuminated area comprises a non-illuminated center portion overlapping the fiber optic axis.

In an embodiment wherein the shaped fiber optic tip is formed of quartz, the shaped fiber optic tip may comprise a diameter of about 250 microns, which exemplary diameter may be suitable for, in one application, a root canal procedure. In an embodiment wherein the shaped fiber optic tip is formed of sapphire, the shaped fiber optic tip may comprise an exemplary diameter of about 750 microns, suitable, as an example, for root canal procedures.

In accordance with an aspect of the present invention, the side-firing output ends described herein may be used for caries removal from predetermined locations (e.g., side walls) of tooth cavities. Using the side-firing output ends of the present invention, undercuts may be effectively generated in caries procedures wherein each undercut may comprise a removed volume of caries defining a reverse-mushroom shaped aperture in the tooth which has a size at the surface of the tooth that is less than sizes of the aperture beneath the surface and which is to be filled with amalgam. Sizes of the aperture of such an undercut may progressively increase with distance away from the tooth surface in a direction toward a center of the tooth. For example, a dentist may insert a curved stainless steel probe into a cavity, detect caries material on a surface (e.g., sidewall) of the cavity, remove the curved stainless steel probe, insert a shaped fiber optic tip of the present invention having a side-firing output end into the cavity, position the side-firing output end to ablate the detected caries material, activate a laser to remove the detected caries material, and then (optionally) repeat the process until all detectable or a desired level of caries material has been removed. The shaped fiber optic tips of the present invention, and in particular their side-firing output ends, can thus facilitate generation of reverse-mushroom shaped apertures by way of operation of their side-firing characteristics, which can facilitate, for example, removal of tissue (e.g., caries) from side walls of the cavity down beneath the surface of the tooth.

Figure 10B:
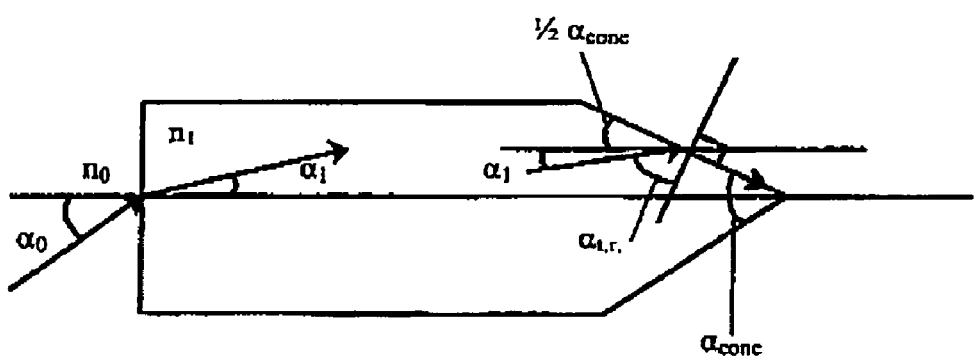
FIG. 10b shows use of the Snell's Refraction Law to calculate cone angle of a fiber optic end of the radiation emitting apparatus.

In accordance with another aspect of the present invention, dimensions of the side-firing output ends of the shaped fiber optic tips can be selected to obtain total or substantially total internal reflection within the shaped fiber optic tip at, for example, the tip/air interface, as elucidated for example in FIG. 10b. With reference to this figure in the context of an exemplary, conically-shaped, side-firing output end, the full angle (i.e., total cone angle) at a distal region of the side-firing output end (e.g., cone) can be in the range from 10 degrees to 170 degrees, and more preferably between 50 degrees and 100 degrees. The shaped fiber optic tip can be a single fiber optic or in modified embodiments a bundle or fused bundle. Generally, the shaped fiber optic tip can have a diameter between 50 and 2000 microns, and can have a numerical aperture (N.A.) depending on the material. The exemplary shaped fiber optic tip can be made of silica or other materials, such as sapphire, or other materials disclosed in U.S. Pat. No. 5,741,247, the entire contents of which are incorporate by reference herein, and can also comprise a hollow waveguide in modified embodiments. In the exemplary embodiment of FIG. 10b, the shaped fiber optic tip comprises a 600 micron core diameter, a numerical aperture of 0.39, an acceptance angle, $\alpha_1$, of 15.6 degrees, and a full cone angle of 60 degrees to 62 degrees.

The full cone angle can be determined using, for example, Snell's Law of Refraction, $n_0 \sin(\alpha_0) = n_1 \sin(\alpha_1)$, for all waveguide modes to experience total internal reflection on at least one of the tapered surfaces of the side-firing output end before exiting through the side-firing output end. More particularly, in the exemplary embodiment of FIG. 10b, the cone comprises a first tapered surface (shown near top of drawing page) and an opposing second tapered surface (shown near bottom of drawing page). According to an implementation of the present invention in which total internal reflection occurs, all light striking the first tapered surface is reflected toward and exits through the second tapered surface to thereby achieve a side-firing effect. In the illustrated example, the refractive indices $n_0$ and $n_1$ can be 1.0 and 1.45, respectively, corresponding to an implementation of a quartz conical side-firing output end transmitting into air, and further values may be implemented wherein $\alpha_0 = 8.0$ degrees and $\alpha_1 = 5.5$ degrees. Beginning with an equation that $(\frac{1}{2})\alpha_{cone} + \alpha_1 + \alpha_{t.r.} = 90$ degrees, wherein $\alpha_{cone}$ is defined as the total cone angle and $\alpha_{t.r.}$ is defined as the angle for total internal reflection, the angle for total internal reflection, $\alpha_{t.r.}$, can be isolated to yield $\alpha_{t.r.} = \sin^{-1}(n_0/n_1)$ which in the present example equals 43.6 degrees. When $(\frac{1}{2})\alpha_{cone} = 40.9$ degrees, the total cone angle can be determined in the example as $\alpha_{cone} = 81.8$ degrees.

Although the full cone angle in the illustrated embodiment of a cone is selected to facilitate total internal reflection, modified embodiments of cones (e.g., having other shapes or materials) or other side-firing output ends may be constructed wherein the internal reflection (i.e., reflection off of a first surface or first tapered surface, or the percentage of reflection from light first striking any tapered or other surface of the side-firing output end) is about 90% or greater. In still other embodiments, a total angle can be constructed to provide for an internal reflection of at least 75%. In further embodiments, however, other varying amounts of internal reflection can be implemented.

In an implementation of a quartz conical side-firing output end transmitting into water, the side-firing output end may be constructed to have a full angle of about 36 degrees, and in an implementation of a quartz conical side-firing output end transmitting into air, the side-firing output end may be constructed to have a full angle of about 82 degrees. In an implementation of a sapphire conical side-firing output end transmitting into water, the side-firing output end may be constructed to have a full angle of about 76 degrees, and in an implementation of a sapphire conical side-firing output end transmitting into air, in order to achieve a similar side-firing effect the side-firing output end may be constructed to have a larger full angle, such as, in the present example, about 104 degrees (as a result, generally, of the divergence angle being greater for air than water).

FIG. 11 is cross-sectional view of a shaped fiber optic tip comprising a symmetric, conical, side-firing output end which is constructed similarly to that of FIG. 10a and which is shown operated in an aqueous environment. The aqueous environment may comprise any combination of fluid (e.g., air) and liquid (e.g., water), such as a submerged liquid environment, or a sprayed or atomized liquid in air embodiment such as disclosed in, for example, U.S. Pat. No. 5,741,247 and the references cited therein. As used herein, the term "aqueous" should not be limited to denoting only water as other liquids in addition to or as an alternative to water may be used. Dimensions of the side-firing output ends of the shaped fiber optic tip can be selected to obtain total or substantially total internal reflection within the shaped fiber optic tip at the tip/aqueous interface. In the illustrated embodiment, the cone angle facilitates both total internal reflection (forming an illuminated ring pattern) and refraction (forming an illuminated center spot) at the tip/aqueous interface of the side-firing output end.

FIG. 10c is cross-sectional view of a shaped fiber optic tip comprising an asymmetric conical side-firing output end in accordance with another embodiment of the present invention. The embodiment of FIG. 10c can be viewed as a combination of the embodiments of FIG. 10a and FIG. 10d and, accordingly, may be constructed for uses, or to favor uses, of either or both of those embodiments. In a representative embodiment wherein the side-firing output end is polished to a non-symmetrical conical shape as shown, all beams of laser radiation exit from the side-firing output end at relatively high angles of up to 90 degrees with respect to the fiber optic axis. Consequently, an off-axis or non-centered dark "blind spot" is formed in front of the side-firing output end such that the output beam pattern or illuminated area comprises an asymmetric ring of laser radiation at the target plane. During formation, a distal end of the shaped fiber optic tip, comprising, for example, sapphire, diamond, or quartz, may be positioned onto an operative surface of a polishing machine, and orientated during polishing in a manner to form the distal end of the shaped fiber optic tip into an asymmetric conical side-firing output end.

In an embodiment wherein the shaped fiber optic tip is formed of quartz or sapphire, the shaped fiber optic tip may have diameters of about 250 microns or 750 microns, respectively, which exemplary diameters may be suitable for, in certain applications, root canal procedures. In implementations of quartz side-firing output ends transmitting into water or air, the side-firing output ends may be constructed to have full angles of about 32 degrees or 40 degrees, respectively. In implementations of sapphire side-firing output ends transmitting into water or air, the side-firing output ends may be constructed to have a full angles of about 36.5 degrees or 52 degrees, respectively.

FIG. 10d is a cross-sectional view of a one-side firing tip comprising a shaped fiber optic tip having a bevel-cut side-firing output end according to a modified embodiment of the present invention, wherein the bevel cut tapers in an output direction of propagation of electromagnetic radiation. In a typical embodiment, the side-firing output end comprises a material such as sapphire, diamond or quartz that is polished to a bevel-cut shape. For example, the shaped fiber optic tip may be grasped and moved to position a distal end thereof onto an operative surface of a polishing machine, with the distal end of the shaped fiber optic being oriented with respect to the operative surface, and not rotated, to remove portions of and polish the distal end of the shaped fiber optic tip into a bevel-cut side-firing output end. Dimensions of the side-firing output ends of the shaped fiber optic tips can be selected to obtain total or substantially total internal reflection of electromagnetic radiation at one side and firing through the opposite bevel-cut side of the side-firing output end of the shaped fiber optic tip.

In accordance with one aspect of the present invention, all beams of laser radiation exit from the bevel-cut side-firing output end at relatively high angles of up to 90 degrees with respect to the fiber optic axis. Consequently, as presently illustrated in the example of a bevel-cut side-firing output end transmitting into air, a dark "blind spot" is formed in front of the side-firing output end such that the output beam pattern or illuminated area comprises a crescent-shaped illuminated portion juxtaposed next to an enlarged, off-center, non-illuminated portion. In an embodiment wherein the shaped fiber optic tip is formed of quartz, the shaped fiber optic tip may have a diameter of about 400 microns to about 600 microns which exemplary diameter range may be suitable for, in one application, cavity preparation procedures in which the shaped fiber optic tip can be flexed and fitted into periodontal pockets. In an embodiment wherein the shaped fiber optic tip is formed of sapphire, the shaped fiber optic tip may have an exemplary diameter of about 750 microns suitable, as an example, for cavity preparation procedures.

In various implementations of quartz or sapphire bevel-cut side-firing output ends that are to be transmitting into water or air, the side-firing output ends may be constructed to have full angles of, for example, about 45 degrees. In such examples involving full angles of about 45 degrees, undercuts may be effectively generated in caries procedures wherein each undercut may comprise a removed volume of caries defining a reverse-mushroom shaped aperture in the tooth as described above. According to other implementations, as a result, generally, of the divergence angle, indicated by dashed lines in the figure, being greater for sapphire than for quartz, in order to obtain a similar side-firing effect for a quartz shaped fiber optic tip, the full angle of the side-firing output end formed of sapphire will be smaller than that of a quartz embodiment. Similarly, according to other embodiments, as a result, generally, of the divergence angle for implementations involving transmission into air being greater than for implementations involving transmission into water, in order to obtain a similar side-firing effect for an air-transmission application, the full angle of the side-firing output end for air-transmissions will be smaller (yielding a more pointed tip) than that used for water-transmission applications. According to further implementations, as a result, generally, of the divergence angle being greater for sapphire than for quartz and the divergence angle being greater for air than water, a bevel-cut side-firing output end formed of quartz and transmitting electromagnetic radiation into water will have an even smaller full angle (producing a more pointed tip) to achieve a similar side-firing effect.

FIG. 12a is an exploded, cross-sectional view of a multi-capillary shaped fiber optic tip, and FIG. 12b is a cross-sectional view of the multi-capillary shaped fiber optic tip similar to that of FIG. 12a in an assembled state. The components forming the multi-capillary shaped fiber optic tip may comprise any combination of materials such as, for example, sapphire, diamond, or quartz.

The distal fiber optic can be glued and/or press fitted into the intermediate-diameter cylindrical fiber optic, and the intermediate diameter cylindrical fiber optic can be glued and/or press fit into the large-diameter cylindrical fiber optic. Regarding the distal fiber optic, it can have an outer diameter of about 200 microns, and can be fabricated without (FIG. 12a) or with (FIG. 12b) a shaped side-firing end such as one of the ends depicted in FIGS. 10a, 10c or 10d. The embodiment of FIG. 12b shows the distal fiber optic comprising a conical side-firing output end, and further shows the intermediate-diameter cylindrical fiber optic and the large-diameter cylindrical fiber optic conduct electromagnetic radiation and providing side-firing effects from their distal ends. Regarding the intermediate-diameter cylindrical fiber optic and the large-diameter cylindrical fiber optic, the former can have an inner diameter of about 200 microns and an outer diameter of about 400 microns and the latter can have an inner diameter of about 400 microns and an outer diameter of about 600 microns.

FIG. 13 is a cross-sectional view of a shaped fiber optic tip implementing a tapered side-firing output end. The structure may comprise, for example, quartz, and may be formed, for example, by heating a conical distal tip to a glass transition temperature and then elongating (e.g., pulling) the distal tip distally, using for example chucks, to deform the structure into that shown in FIG. 13. In a typical embodiment the shaped fiber optic tip can have a maximum outer diameter of about 800 microns (near the proximal end of the illustrated embodiment) and a minimum diameter of about 100 microns (near the distal, side-firing end of the illustrated embodiment).

Although shown as a solid structure, the shaped fiber optic tip may comprise a hollow (e.g., resembling part or all of the structures/functions of FIGS. 14a and 14b, infra), or partially hollow (e.g., resembling part or all of the structures/functions of FIGS. 15a and 15b, infra), structure in modified embodiments. For example, the shaped fiber optic may comprise a hollow or partially hollow interior surrounded by an outer sidewall, which sidewall defines the shape shown in FIG. 13, or slightly modified shapes thereof, and which sidewall may or may not comprise a waveguide. The sidewall may comprise, for example, a uniform or substantially uniform thickness. The slightly modified shapes may comprise, for example, embodiments which have fewer or less-pronounced curves and consequently shapes resembling combinations of the shape shown in FIG. 13 and a cylindrical shape. According to other embodiments, the slightly modified shapes may comprise, for example, embodiments which have greater or more-pronounced curves and consequently shapes having greater variations in diameter along the fiber optic axis (along any part, parts, or all of the fiber optic axis) than that shown in FIG. 13. In certain embodiments, the hollow or partially hollow shaped fiber optic tip may be configured, with or without the sidewall operating as a waveguide, to have structure and/or to operate, in whole or in part, according to one or more of the implementations depicted and described in connection with the following FIGS. 14a, 14b, 15a and 15b, or combinations thereof, to the extent functional, as will be apparent to one skilled in the art in light of the present disclosure. According to particular implementations, the shaped fiber optic tip may be left substantially unchanged in shape, or alternatively modified in shape, and provided with and operated in accordance with a peripheral (e.g., annular at any cross-sectional location along the fiber optic axis, or, in other words, conforming to the shape shown in FIG. 13) fluid movement path as described in connection with the following FIGS. 15a and 15b. Thus, in an exemplary construction, the peripheral fluid movement path may comprise, for example, a surgical stainless steel sleeve or cannula that conforms to the unaltered (or, alternatively, altered) surface of the shaped fiber optic tip of FIG. 13.

Figure 14A:
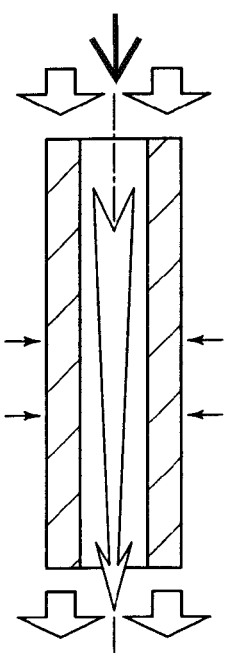
FIG. 14a is a cross-sectional view of a fluid-movement fiber optic tip having a concentric waveguide encircling a central fluid-delivery path, which is shown being operated in an application mode.
Figure 14B:
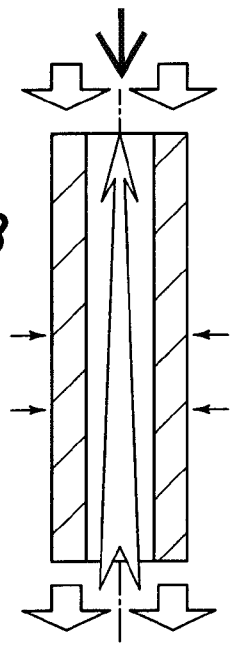
FIG. 14b is a cross-sectional view of the fluid-movement fiber optic tip of FIG. 14a with the central fluid-delivery path being operated in an evacuation mode.

FIG. 14a is a cross-sectional view of a fluid-movement fiber optic tip comprising a concentric waveguide, e.g., a non-interrupted volume, encircling a central fluid-delivery path. The fluid-movement fiber optic tip is shown being operated in an application mode wherein an aqueous environment is supplied by way of a source of positive pressure (cf. downwardly directed arrow within central fluid-delivery path) through and output from a distal end of the central fluid-delivery path. FIG. 14b is a cross-sectional view of a fluid-movement fiber optic tip similar to that of FIG. 14a with a central fluid-delivery path being operated in an evacuation mode wherein materials (e.g., an aqueous environment and/or liquids from a treatment site) are drawn into a distal end of the central fluid-delivery path for removal thereof by way of a source of negative pressure (cf. upwardly directed arrow within central fluid-delivery path). The components forming the fluid-movement fiber optic tip may comprise materials such as, for example, sapphire, diamond, quartz, or combinations thereof. In the illustrated embodiment, a distal end of the concentric waveguide is coterminous with a distal end of the central fluid-delivery path, but in other embodiments either of the concentric waveguide and the central fluid-delivery path may extend distally past a distal end of the other. The fluid-movement fiber optic tip may comprise, in an illustrated embodiment, a hollow waveguide fiber optic tip, such as, for example, the large-diameter cylindrical fiber optic disclosed above in connection with FIGS. 12a and 12b. In one embodiment, the fluid-movement fiber optic tip can have the same or similar dimensions as set forth above to describe the large-diameter cylindrical fiber optic, and in another embodiment the fluid-movement fiber optic tip can have an inner diameter of about 500 microns and an outer diameter of about 800 microns. In yet another embodiment, the fluid-movement fiber optic tip can have an inner diameter of about 300 microns and an outer diameter of about 600 microns.

Application of positive pressure to supply the aqueous (or other) environment and of negative pressure to evacuate materials from an area in proximity to the distal end can be provided through one or more of proximal ends of the central fluid-delivery paths, apertures formed (e.g., drilled) into sidewalls of the concentric waveguides as indicated in phantom in the figures, or combinations thereof. In modified embodiments, one or more of the apertures (and/or the proximal end of the central fluid-delivery path, in any combination) may be dedicated to either supplying the aqueous environment to or evacuating materials from the central fluid-delivery path. For instance, the four apertures shown in phantom in FIG. 14a may be used to deliver an aqueous environment to the central fluid-delivery path at first points in time, and the four apertures shown in phantom in FIG. 14b may be used to remove materials from the central fluid-delivery path at second points in time. In one implementation, one or more apertures disposed in the sidewall of the concentric waveguide delivers an aqueous environment to the central fluid-delivery path at first points in time, and a proximal end of the central fluid-delivery path removes materials from the central fluid-delivery path at second points in time. Generally, such apertures may be formed anywhere along the lengths of the fluid-movement fiber optic tips, at any orientations, according to desired functions and applications. For example, it may be advantageous to form apertures for delivering an aqueous environment closer to the distal end of the central fluid-delivery path and/or at orientations to inject the aqueous environment to move distally within the central fluid-delivery path. In other embodiments, it may additionally or alternatively be advantageous to orient one or more of the aqueous-environment injecting apertures to inject the aqueous environment into the central fluid-delivery path so as to have a swirl component wherein, for example, the aqueous environment is caused to swirl about the fiber optic axis as it travels distally through the central fluid-delivery path. Application of positive pressure to supply the aqueous (or other) environment and of negative pressure to evacuate materials from an area in proximity to the distal end can be provided using any timing sequence and/or can be coordinated in any way with electromagnetic radiation being provided through the concentric waveguide of the fluid-movement fiber optic tip. All timing and operational permutations are contemplated as will be apparent to those skilled in the art. In one implementation, electromagnetic radiation is provided through the central fluid-delivery path in addition to or as an alternative to being delivered through the concentric waveguide by way of one or more sources of electromagnetic radiation (cf. downwardly-directed arrows pointing into the fluid-movement fiber optic tip). In another implementation, electromagnetic radiation having a first characteristic is provided through the central fluid-delivery path and concentrated (i.e., other than mere ambient light) electromagnetic radiation having a second characteristic is delivered through the concentric waveguide. For example, the electromagnetic radiation having a first characteristic can comprise laser energy provided from a source of concentrated electromagnetic radiation (cf. downwardly-directed solid arrow pointing into the fluid-movement fiber optic tip) through the central fluid-delivery path, and the electromagnetic radiation having a second characteristic can comprise white light such as generated by an LED and provided by way of another source of electromagnetic radiation (cf. downwardly-directed non-solid arrows pointing into the fluid-movement fiber optic tip) through the concentric waveguide, or visa versa. In certain embodiments wherein electromagnetic radiation is provided through the central fluid-delivery path (and, optionally, also through the concentric waveguide), a wavelength of the electromagnetic radiation may be selected to be highly absorbed by one or more components in the aqueous environment with the electromagnetic radiation being applied during application modes to assist distal movement of the aqueous environment through the central fluid-delivery path. For example, the aqueous environment may comprise atomized particles of water and the electromagnetic radiation may comprise laser energy from a laser having a wavelength (e.g., about 3 microns) that is highly absorbed by the water as disclosed, for example, in U.S. Pat. No. 5,741, 247. This patent describes, for example, electromagnetic energy sources comprising wavelengths within a range from about 2.69 to about 2.80 microns and wavelengths of about 2.94 microns, and further describes lasers comprising one or more of Er:YAG, Er:YSGG, Er, Cr:YSGG and CTE:YAG lsaers. In such a configuration as descried in U.S. Pat. No. 5,741,247,water particles within the central fluid-delivery lumen can be contacted with the electromagnetic radiation, reacting (e.g., expanding) and being accelerated distally out of the central fluid-delivery lumen. As an example of various possible timing protocols, one or more pulses of aqueous environment can be introduced into the central fluid-delivery lumen followed by introduction of one or more pulses of electromagnetic energy into the central fluid-delivery lumen, with the sequence then repeated. In another implementation, the aqueous environment may comprise atomized particles of water and the electromagnetic radiation may comprise laser energy from a laser having a wavelength (e.g., about 1 micron) that is not highly absorbed by the water, in which case one or more pulses of aqueous environment (e.g., atomized particles or a stream of water) can be introduced into the central fluid-delivery lumen commensurate in time (or, alternatively, intermittently) with introduction of one or more pulses of electromagnetic energy into the central fluid-delivery lumen, with the sequence then being repeated.

Figure 15A:
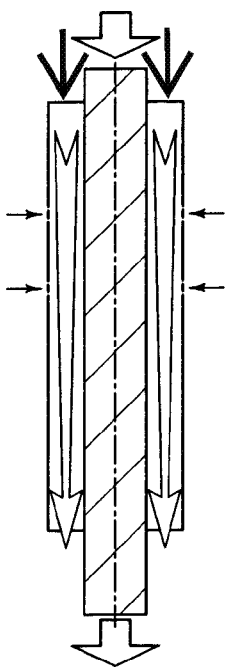
FIG. 15a is a cross-sectional view of a fluid-movement fiber optic tip having a central waveguide encircled by an peripheral (e.g., annular) fluid-delivery path, which is shown being operated in an application mode.
Figure 15B:
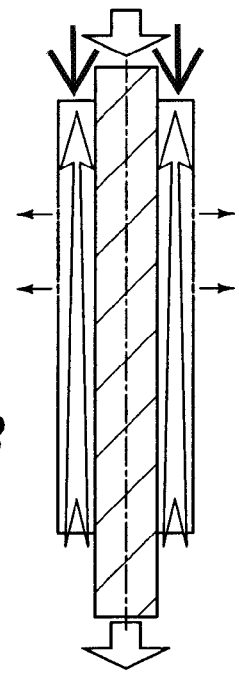
FIG. 15b is a cross-sectional view of the fluid-movement fiber optic tip of FIG. 15a with the peripheral fluid-delivery path being operated in an evacuation mode.

FIG. 15a is a cross-sectional view of a fluid-movement fiber optic tip comprising a peripheral (e.g., annular) fluid-movement path encircling a central waveguide. The fluid-movement fiber optic tip is shown being operated in an application mode wherein an aqueous environment is supplied by way of a source of positive pressure (cf. downwardly directed arrows within fluid-movement path) through and output from a distal end of the annular fluid-movement path. FIG. 15b is a cross-sectional view of a fluid-movement fiber optic tip similar to that of FIG. 15a with an annular fluid-movement path being operated in an evacuation mode wherein materials (e.g., an aqueous environment and/or liquids from a treatment site) are drawn into a distal end of the annular fluid-movement path for removal thereof by way of a source of negative pressure (cf. upwardly directed arrows within annular fluid-movement path). The fluid-movement fiber optic tip may comprise, in an illustrated embodiment, a central waveguide comprising, for example, sapphire, diamond, quartz, or combinations thereof, surrounded by a sidewall (e.g., cannula) which may comprise, for example, surgical stainless steel. In modified embodiments, a distal end of the central waveguide can be constructed to have, and/or to be operated in accordance with, descriptions of the shaped fiber optic tips of one or more of FIGS. 10a, 10c, 10d, 11, 12b, or combinations thereof. In the illustrated embodiment, the distal end of the central waveguide extends beyond a distal end of the annular fluid-movement path, but in other embodiments the distal end of the annular fluid-movement path may be coterminous with or extend past the distal end of the central waveguide. According to a typical embodiment, the central waveguide may comprise a fiber optic having an outer diameter of about 600 microns, and the annular fluid-movement path may have dimensions of 1200 microns.

Application of positive pressure to supply the aqueous (or other) environment and of negative pressure to evacuate materials from an area in proximity to the distal end can be provided through one or more of proximal ends of the annular fluid-movement paths, apertures formed (e.g., drilled) into sidewalls (e.g., cannulas) of the annular fluid-movement paths as indicated in phantom in the figures, or combinations thereof. In modified embodiments, one or more of the apertures (and/or the proximal end of the annular fluid-movement path, in any combination) may be dedicated to either supplying the aqueous environment to or evacuating materials from the annular fluid-movement path. For instance, the four apertures shown in phantom in FIG. 15a may be used to deliver an aqueous environment to the annular fluid-movement path at first points in time, and the four apertures shown in phantom in FIG. 15b may be used to remove materials from the annular fluid-movement path at second points in time. In one implementation, one or more apertures disposed in a sidewall of the annular fluid-movement path delivers an aqueous environment to the annular fluid-movement path at first points in time, and a proximal end of the annular fluid-movement path removes materials from the annular fluid-movement path at second points in time. Generally, such apertures may be formed anywhere along the lengths of the fluid-movement fiber optic tips, at any orientations, according to desired functions and applications. For example, as discussed above in connection with FIGS. 14a and 14b, it may be advantageous to form apertures for delivering an aqueous environment closer to the distal end of the annular fluid-movement path and/or at orientations to inject the aqueous environment to move distally within the annular fluid-movement path. Likewise, in other embodiments, it may additionally or alternatively be advantageous to orient one or more of the aqueous-environment injecting apertures to inject the aqueous environment into the annular fluid-movement path so as to have a swirl component wherein, for example, the aqueous environment is caused to swirl about the fiber optic axis as it travels distally through the annular fluid-movement path. As with FIGS. 14a and 14b, application of positive pressure to supply the aqueous (or other) environment and of negative pressure to evacuate materials from an area in proximity to the distal end can be provided using any timing sequence and/or can be coordinated in any way with the provision of electromagnetic radiation through the central waveguide of the fluid-movement fiber optic tip, and all timing and operational permutations that will be apparent to those skilled in the art upon reading this disclosure are contemplated.

In one implementation, electromagnetic radiation is provided through the annular fluid-movement path in addition to or as an alternative to being delivered through the central waveguide by way of one or more sources of electromagnetic radiation (cf. downwardly directed arrows pointing into the fluid-movement fiber optic tip). In another implementation, electromagnetic radiation having a first characteristic is provided from a source of concentrated electromagnetic radiation (cf. downwardly-directed solid arrows pointing into the fluid-movement fiber optic tip) through the annular fluid-movement path and electromagnetic radiation having a second characteristic is delivered by way of another source of electromagnetic radiation (cf. downwardly-directed non-solid arrow pointing into the fluid-movement fiber optic tip) through the central waveguide. For example, the electromagnetic radiation having a first characteristic can comprise white light generated by an LED provided through the annular fluid-movement path, and the electromagnetic radiation having a second characteristic can comprise laser energy provided through the central waveguide, or visa versa. In certain embodiments wherein electromagnetic radiation is provided through the annular fluid-movement path (and, optionally, also through the central waveguide), a wavelength of the electromagnetic radiation may be selected to be highly absorbed by one or more components in the aqueous environment with the electromagnetic radiation being applied during application modes to assist distal movement of the aqueous environment through the annular fluid-movement path. For example, the aqueous environment may comprise atomized particles of water and the electromagnetic radiation may comprise laser energy from a laser having a wavelength (e.g., about 3 microns) that is highly absorbed by the water as disclosed, for example, in U.S. Pat. No. 5,741,247. In such a configuration, water particles within the annular fluid-movement path can be contacted with the electromagnetic radiation, reacting (e.g., expanding) and being accelerated distally out of the central fluid-movement lumen. As an example of various possible timing protocols, one or more pulses of aqueous environment can be introduced into the annular fluid-movement path followed by introduction of one or more pulses of electromagnetic energy into the annular fluid-movement path, with the sequence then repeated. In another implementation, the aqueous environment may comprise atomized particles of water and the electromagnetic radiation may comprise laser energy from a laser having a wavelength (e.g., about 1 micron) that is not highly absorbed by the water, in which case one or more pulses of aqueous environment (e.g., atomized particles or a stream of water) can be introduced into the annular fluid-movement path commensurate in time (or, alternatively, intermittently) with introduction of one or more pulses of electromagnetic energy into the annular fluid-movement path, with the sequence then being repeated.

According to various contemplated embodiments, the cannula defining the annular fluid-movement path may comprise uniform or non-uniform thicknesses and/or may be spaced at uniform or non-uniform distances from an outer surface of the central waveguide, at various points along a length of the fiber optic axis of the fluid-movement fiber optic tip. For example, the cannula may comprise a substantially uniform thickness and may be spaced at progressively smaller distances from the outer surface of the central waveguide in a direction from the proximal end to the distal end along a length of the fiber optic axis of the fluid-movement fiber optic tip.

Regarding the side-firing output ends of the shaped fiber optic tips of FIGS. 10a, 10c, 10d, 11 and 12b, any of these output ends may be modified or otherwise formed to have non-cylindrical shapes, such as spherical, chiseled, or other light-intensity altering (e.g., dispersing) shapes, in additional embodiments.

Also, regarding the side-firing output ends of the shaped fiber optic tips of FIGS. 10a, 10c, 10d, 11 and 12b, any of these output ends further can be modified by removing parts of the distally-disposed output ends to yield, for example, truncated-cone or truncated-bevel distal ends that provide end-firing components. As examples, shaped fiber optic tips having diameters of about 600 microns to about 750 microns may be formed (e.g., polished) to have truncated planar output surfaces of about 200 microns in diameter, and shaped fiber optic tips having diameters of about 200 microns may be formed (e.g., polished) to have truncated planar output surfaces of about 50 microns in diameter.

For example, planar output surfaces centered on and perpendicular to longitudinal axes of the fiber optics can be formed. In the implementation of FIG. 10a, for example, the pointed end of the conical tip, which in the illustrated embodiment is centered on the longitudinal optical axis of the fiber optic, can be polished flat to yield a planar output surface so that light traveling along the optical axis exits the planar output surface and continues to travel, unrefracted, along the optical axis. Thus, in the described implementation, the planar output surface is oriented to be perpendicular with, and to intersect with, the longitudinal axis of the fiber optic.

As another implementation, the beveled, side-firing output end of the construction of FIG. 1c, which in the illustrated embodiment is not centered on the longitudinal optical axis of the fiber optic, can be polished to form a planar output surface so that light traveling in a direction parallel to the optical axis exits the planar output surface and continues to travel, unrefracted, in a direction parallel to the optical axis. Thus, the planar output surface is again oriented to be perpendicular with, but not to intersect with, the longitudinal axis of the fiber optic.

Regarding the side-firing output ends of the shaped fiber optic tips of FIGS. 10a, 10c, 10d, 11 and 12b, any of these tips and output ends may be modified or otherwise formed to have hollow interiors defining central fluid-delivery paths such as those described in connection with FIGS. 14a and 14b, and/or operated as such in whole or in part as described in connection with FIGS. 14a and 14b. In exemplary implementations, the hollow interiors may be centered along fiber optic axes of the shaped fiber optic tips and/or may be aligned with what would otherwise be the planar output surfaces so that the planar output surfaces are not surfaces but rather are output openings of the hollow interiors.

In other implementations, the modified output ends (e.g., planar output surfaces) may have other orientations which are not perpendicular to the optical axes of the fiber optics, and in still further implementations the modified ends may comprise curved, rounded, or other non-planar surfaces.

The modified output ends (e.g., planar output surfaces) can generate output beam patterns similar to those depicted in FIGS. 10a, 10c, 10d and 12b but with filled center portions as a result of laser energy passing through, unrefracted, the planar output surfaces. The shapes and intensities of the filled center portions in the output beam patterns, resulting from implementations of the modified output ends, can be changed by changing characteristics (e.g., diameter and/or surface characteristics) as will be recognized by one skilled in the art in light of this disclosure.

The filled center portion generated by incorporating a modified output end (e.g., planar output surface) into the construction of the shaped fiber optic tip of FIG. 11 will comprise, when used in an aqueous environment as shown, a filled center portion of one or more of greater size and greater intensity, as a result of laser energy passing through, unrefracted, the planar output surface.

Accordingly, the modified output ends can provide end-firing components to the side-firing output ends of the fiber optics thus generating more uniform output beam patterns. Such side-firing, end-firing combination fiber optic tips can have applicability in procedures where it is desired to irradiate sidewalls and bottom layers of a target surface. For example, the modified output ends may have applicability for periodontal pocket procedures wherein it may be desired to direct radiation to sidewalls and to the bottom surfaces during modification or removal of the periodontal pocket area.

The above-described embodiments have been provided by way of example, and the present invention is not limited to these examples. Multiple variations and modification to the disclosed embodiments will occur, to the extent not mutually exclusive, to those skilled in the art upon consideration of the foregoing description. Additionally, other combinations, omissions, substitutions and modifications will be apparent to the skilled artisan in view of the disclosure herein. Accordingly, the present invention is not intended to be limited by the disclosed embodiments, but is to be defined by reference to the appended claims.

What is claimed is:

1. A laser handpiece, comprising:
    a shaped fiber optic tip, the shaped fiber optic tip being constructed to deliver electromagnetic radiation supplied from a source of electromagnetic radiation to a vicinity outside of the shaped fiber optic tip and the shaped fiber optic tip having an interior coupled to a source of positive pressure to provide pressure to the interior of the shaped fiber optic tip, wherein the electromagnetic radiation and the positive pressure are emitted to the vicinity with the electromagnetic radiation having a wavelength and energy distribution suitable for cutting or ablating one or more of hard tissue and soft tissue, wherein a spatial energy distribution of electromagnetic radiation emitted from the shaped fiber optic tip has an energy peak in an area other than along an optical axis of the shaped fiber optic tip; and
    a source of negative pressure coupled to the interior of the shaped fiber optic tip;
    a sidewall surrounding and defining the interior whereby the interior extends through the shaped fiber optic tip in a direction parallel to the optical axis;
    material injecting apertures disposed in the sidewall for delivering an aqueous environment under influence of the positive pressure into the interior whereby the material is delivered into the interior in a fashion to cause it to move at least partially transversely to the optical axis and distally within the interior; and
    a material evacuator disposed proximally of the material injecting apertures for applying negative pressure to the interior under influence of the source of negative pressure to remove material therefrom;
    wherein the source of electromagnetic radiation is coupled to the interior and is configured to direct the electromagnetic energy through the interior distally in a direction parallel to the optical axis.

2. The laser handpiece as set forth in claim 1, the source of positive pressure being coupled to deliver fluid along a path to a vicinity of the shaped fiber optic tip, the path being substantially parallel to the optical axis of the shaped fiber optic tip.

3. The laser handpiece as set forth in claim 2, wherein the source of positive pressure and the path are configured to deliver the fluid to the shaped fiber optic tip as atomized fluid particles.

4. The laser handpiece as set forth in claim 1, wherein:
    the shaped fiber optic tip has a side-firing output end with a non-cylindrical shape; and
    the source of positive pressure is coupled to the side-firing output end.

5. The laser handpiece as set forth in claim 1, wherein the material is an aqueous environment.

6. The laser handpiece as set forth in claim 5, wherein the aqueous environment is caused to swirl about the optical axis as it travels distally through the interior.

7. The laser handpiece as set forth in claim 3, wherein the atomized fluid particles comprise water.

8. The laser handpiece as set forth in claim 1, wherein the electromagnetic energy source is constructed to emit electromagnetic energy that is suitable for cutting a target comprising tooth tissue.

9. The laser handpiece as set forth in claim 1, wherein the electromagnetic energy source comprises one of a wavelength within a range from about 2.69 to about 2.80 microns and a wavelength of about 2.94 microns.

10. The laser handpiece as set forth in claim 1, wherein the electromagnetic energy source comprises one of an Er:YAG, an Er:YSGG, an Er, Cr:YSGG and a CTE:YAG laser.

* * * * *

UNITED STATES PATENT AND TRADEMARK OFFICE
CERTIFICATE OF CORRECTION

PATENT NO.        : 7,620,290 B2
APPLICATION NO.   : 11/033441
DATED             : November 17, 2009
INVENTOR(S)       : Rizoiu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 439 days.

Signed and Sealed this

Twenty-sixth Day of October, 2010

David J. Kappos
*Director of the United States Patent and Trademark Office*